United States Patent
Nelson

(10) Patent No.: US 6,551,498 B2
(45) Date of Patent: Apr. 22, 2003

(54) LOWER PROTECTIVE SHIELD FOR AN EXHAUST SENSOR AND METHOD FOR MAKING THE SAME

(75) Inventor: Charles Scott Nelson, Clio, MI (US)

(73) Assignee: Delphi Technologies, Inc., Troy, MI (US)

( * ) Notice: Subject to any disclaimer, the term of this patent is extended or adjusted under 35 U.S.C. 154(b) by 0 days.

(21) Appl. No.: 09/782,682

(22) Filed: Feb. 13, 2001

(65) Prior Publication Data

US 2002/0134692 A1 Sep. 26, 2002

(51) Int. Cl.⁷ .............................................. G01N 27/407
(52) U.S. Cl. ....................... 205/784.5; 204/424; 204/428
(58) Field of Search ................................. 204/421–429; 205/783–785

(56) References Cited

U.S. PATENT DOCUMENTS

| | | | |
|---|---|---|---|
| 3,864,232 A | * | 2/1975 | Handman et al. |
| 4,132,615 A | * | 1/1979 | Linder et al. |
| 4,186,072 A | * | 1/1980 | Blumenthal et al. |
| 4,272,349 A | * | 6/1981 | Furutani et al. |
| 4,362,605 A |   | 12/1982 | Bozon et al. |
| 4,466,880 A | * | 8/1984 | Torii et al. |
| 4,784,728 A | * | 11/1988 | Capone |
| 4,915,815 A | * | 4/1990 | Shibata et al. |

FOREIGN PATENT DOCUMENTS

| | | |
|---|---|---|
| DE | 4009890 | 10/1991 |
| DE | 40099890 | 12/1991 |
| JP | 61172048 | 8/1986 |
| JP | 63275943 | 11/1988 |
| JP | 63298147 | 12/1988 |
| JP | 02129540 | 5/1990 |
| JP | 0815997 | 6/1996 |

OTHER PUBLICATIONS

Japanese Abstract No. 61172048; Japanese Abstract No. 6327943; Japanese Abstract No. 63298147.
Japanese Abstract No. 02129540; and Japanese Abstract No. 0815997.

* cited by examiner

Primary Examiner—T. Tung
(74) Attorney, Agent, or Firm—Vincent A. Cichosz

(57) ABSTRACT

The protective shield arrangement for an exhaust sensor and method of making and using the same is achieved by providing a protective shield for an exhaust gas sensor that comprises a porous mesh material formed as a cap for placement over an end portion of a sensing element. This is formed by a method that comprises providing a unitary piece of the mesh material, and folding the mesh material to form the cap. Thereby, gas passes through the tortuous pathway created by the mesh material to be sensed by the sensor.

18 Claims, 2 Drawing Sheets

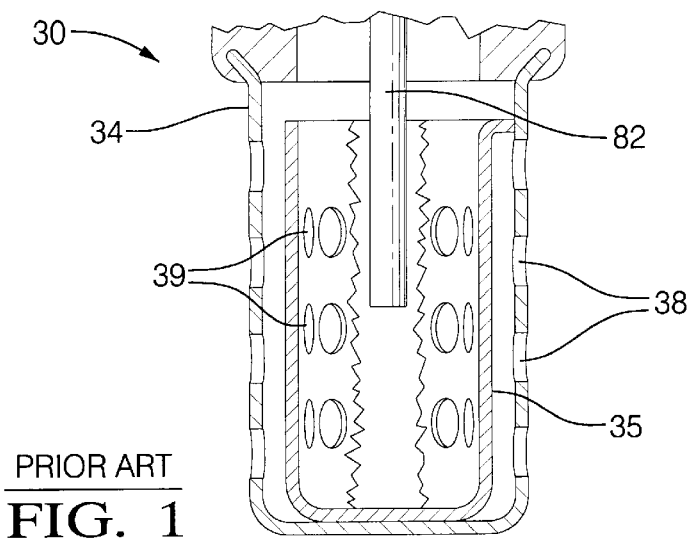
PRIOR ART
FIG. 1
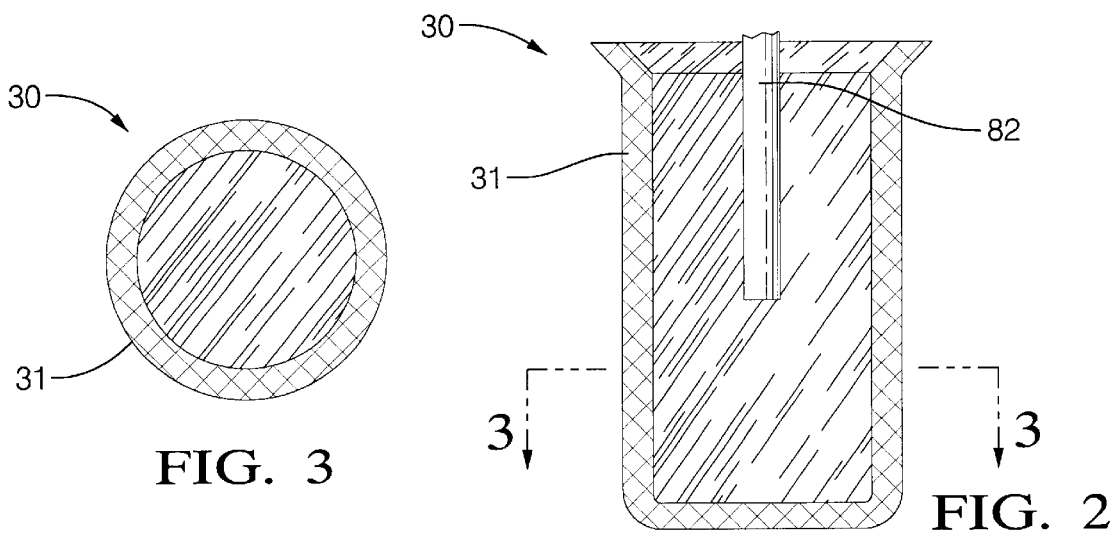
FIG. 3
FIG. 2
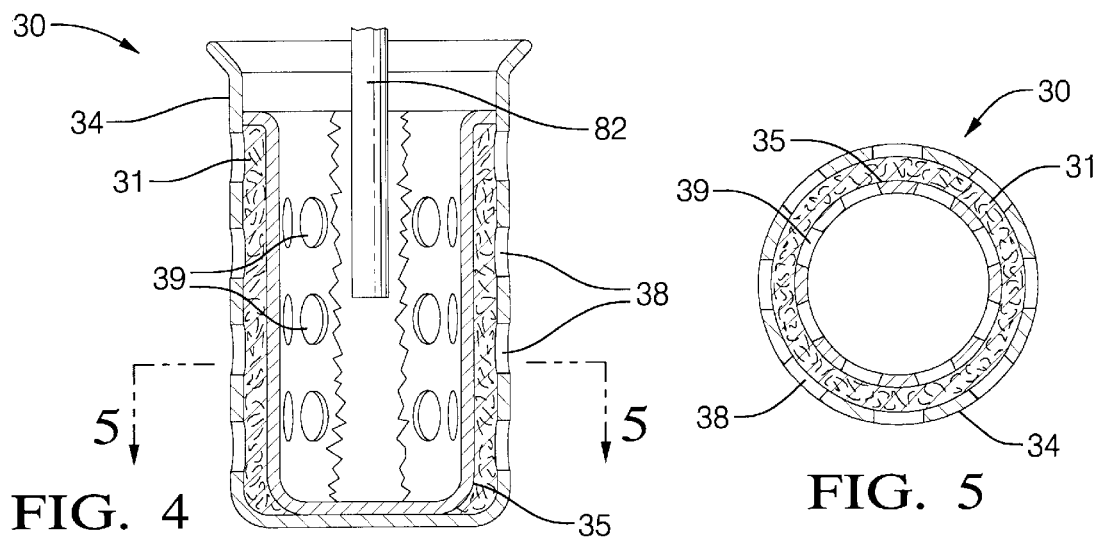
FIG. 4
FIG. 5

LOWER PROTECTIVE SHIELD FOR AN EXHAUST SENSOR AND METHOD FOR MAKING THE SAME

TECHNICAL FIELD

The present invention relates to exhaust gas sensors. More particularly, the present invention relates to an exhaust gas sensor having an lower protective shield and method for making the same.

BACKGROUND OF THE INVENTION

Exhaust sensors are used in a variety of applications that require qualitative and quantitative analysis of gases. For example, oxygen sensors have been used for many years in automotive vehicles to sense the presence of oxygen in exhaust gases, for example, to sense when an exhaust gas content switches from rich to lean or lean to rich. In automotive applications, the direct relationship between oxygen concentration in the exhaust gas and the air-to-fuel ratios of the fuel mixture supplied to the engine allows the oxygen sensor to provide oxygen concentration measurements for determination of optimum combustion conditions, maximization of fuel economy, and the management of exhaust emissions.

A conventional stoichiometric oxygen sensor typically consists of an ionically conductive solid electrolyte material, a porous electrode on the sensor's exterior exposed to the exhaust gases with a porous protective overcoat, and a porous electrode on the sensor's interior surface exposed to a known oxygen partial pressure. Sensors typically used in automotive applications use a yttria stabilized zirconia based electrochemical galvanic cell with porous platinum electrodes, operating in potentiometric mode, to detect the relative amounts of oxygen present in an automobile engine's exhaust. When opposite surfaces of this galvanic cell are exposed to different oxygen partial pressures, an electromotive force is developed between the electrodes on the opposite surfaces of the zirconia wall, according to the Nernst equation:

$$E = \left(\frac{-RT}{4F}\right) \ln\left(\frac{P_{O_2}^{ref}}{P_{O_2}}\right)$$

where:
    $E$ = electromotive force
    $R$ = universal gas constant
    $F$ = Faraday constant
    $T$ = absolute temperature of the gas
    $P_{O_2}^{ref}$ = oxygen partial pressure of the reference gas
    $P_{O_2}$ = oxygen partial pressure of the exhaust gas Due to the large difference in oxygen partial pressures between fuel rich and fuel lean exhaust conditions, the electromotive force changes sharply at the stoichiometric point, giving rise to the characteristic switching behavior of these sensors. Consequently, these potentiometric oxygen sensors indicate qualitatively whether the engine is operating fuel rich or fuel lean, without quantifying the actual air to fuel ratio of the exhaust mixture. Increased demand for improved fuel economy and emissions control has necessitated the development of oxygen sensors capable of quantifying the exhaust oxygen partial pressure over a wide range of air fuel mixtures in both fuel-rich and fuel-lean conditions.

Sensors are typically sealed from the outside environment to prevent water intrusion and environmental contaminants from entering the sensor. Sensors are also typically sealed from the exhaust using high temperature sealing materials (for example, talc or glass) designed to withstand spark-ignition environments (where the exhaust can reach temperatures up to about 1,000° C.). Consequently, great care and time consuming effort must be taken to prevent the sensor's sensing element from being damaged by exhaust, heat, impact, vibration, the environment, etc.

Particularly, an exhaust sensor requires a protective shield (lower shield) around the tip of the sensor element that allows exhaust gas to be sensed while simultaneously protecting the sensor element. Two types of protective shields are commonly used. The first type is a single shield generally having slits to allow for the passage of exhaust gas. Typically, this type of shield is used where precise control of temperature about the sensor element is desired. The second type is a dual shield having both internal and external shields.

A dual shielded protective shield 30 is shown in prior art FIG. 1. Internal shield 35 is disposed within and surrounded by outer shield 34. Within internal shield 35, sensing element lower end 82 is disposed for sensing exhaust gas. Internal shield 35 helps to isolate radiative heat that would affect the sensing element. Also, the internal shield 35 helps to prevent direct impingement from solid and liquid exhaust matter onto the sensing element. To vary the amount of exhaust gas contacting the sensing element, the size, number, and placement of apertures 38 and 39 can be varied. The apertures 38 and 39 are costly to manufacture. The holes are generally made by a punching technique where round disks are removed from a rectangular sheet. The remnant portions, i.e., the disks become waste thereby creating about 40 to about 50% scrap material. As the shields are comprised largely of temperature resistant materials such as nickel, the scrap cost is significant relative to the total cost of the lower shield. In addition to material costs, the tooling costs are significant because the apertures must be punched from the sides of the sheet metal shields without deforming the shield structure.

Accordingly, there remains a need in the art for a low cost, contaminant resistant protective shield arrangement.

SUMMARY OF THE INVENTION

The problems and disadvantages of the prior art are overcome and alleviated by the protective shield arrangement for an exhaust sensor and method of making and using the same. This is achieved by providing a protective shield for an exhaust gas sensor that comprises a porous mesh material formed as a cap for placement over an end portion of a sensing element which is made by a method that comprises providing a unitary piece of the mesh material, and folding the mesh material to form the cap.

Thereafter, the cap can be used as a protective shield by affixing the cap over an end portion of a sensing element of an exhaust sensor; supplying a gas to be sensed; and sensing the gas wherein the sensing comprises supplying the gas to an exterior of the protective shield, passing the gas through a tortuous pathway within the mesh material and into an interior portion of the protective shield, and exposing the sensing element to the gas.

The above-described and other features and advantages of the present invention will be appreciated and understood by those skilled in the art from the following detailed description, drawings, and appended claims.

BRIEF DESCRIPTION OF THE DRAWINGS

The present invention will now be described by way of example with reference to the following Figures, which are meant to be exemplary, not limiting, and in which:

FIG. 1 is a prior art cross-sectional view of a dual shielded protective shield.

FIG. 2 is a cross-sectional view of one embodiment of the present invention illustrating a protective shield comprised of mesh material.

FIG. 3 is an above planar view of the protective shield similar to that depicted in FIG. 2.

FIG. 4 is a cross-sectional view of another embodiment of the present invention illustrating a dual shielded protective shield having mesh material between the inner and outer shields.

FIG. 5 is an above planar view of the protective shield depicted in FIG. 4.

DESCRIPTION OF THE PREFERRED EMBODIMENT

Figure 6:
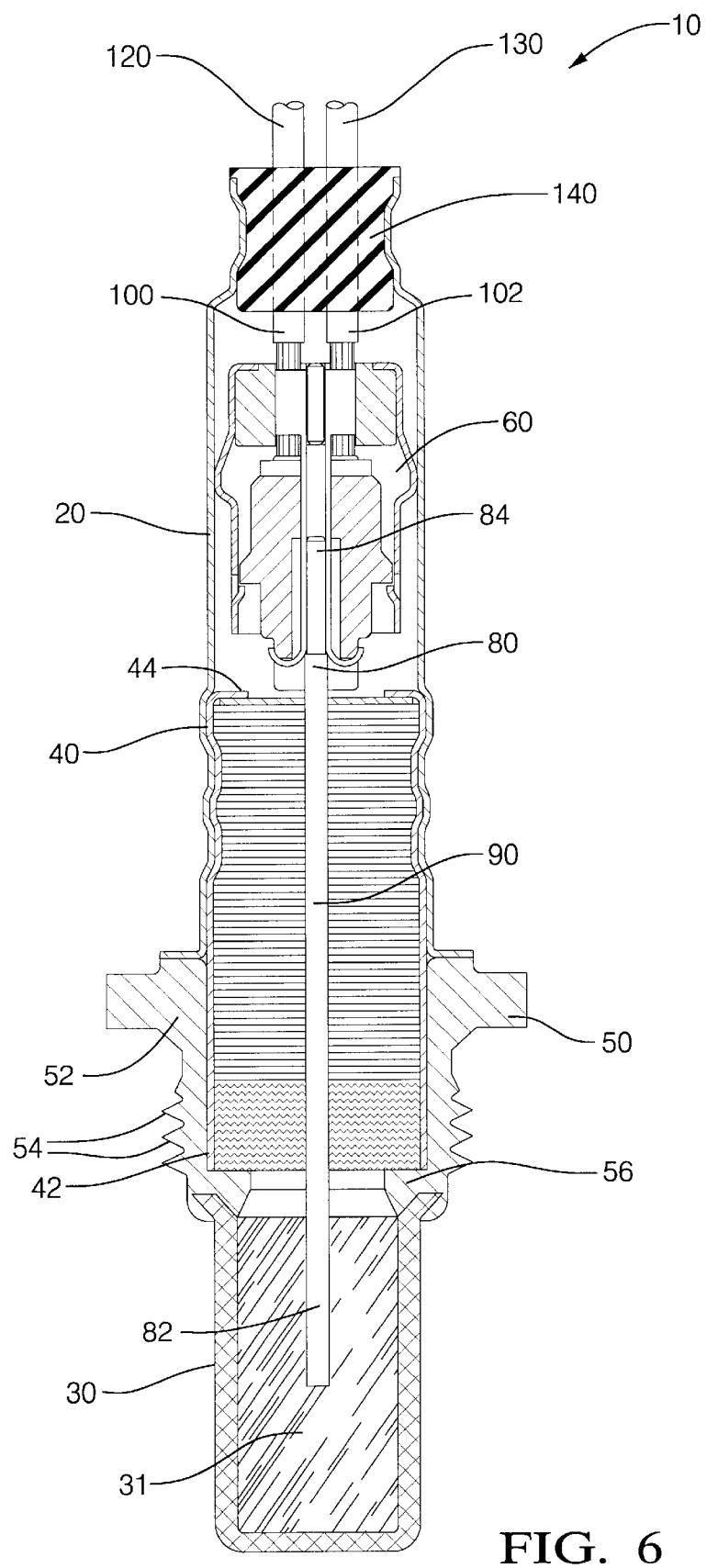
FIG. 6 is a cross-sectional view of an exhaust sensor utilizing the protective shield depicted in FIG. 2.

The protective shield for use with an exhaust gas sensor, as described herein, is comprised of a metal mesh. The mesh shield allows for control of the amount of gas contacting the sensor element while protecting the sensor element from impact or contamination. In the application, protective shield 30 is comprised of a mesh material 31 that can be formed as an overlay in the shape of a round cap as shown in FIG. 2. A protective shield comprising mesh material (mesh shield) is not orientation sensitive as other shapes could be used, e.g., an oval shape multi-sided design or the like. While any porous mesh material that has sufficient strength and can withstand the high temperature of exhaust gas (up to about 1,000° C.) can function as a protective shield, the design is more preferably a metal mesh, and most preferably a stainless steel and/or high nickel content steel mesh.

By altering the size, density, and material properties, a protective shield can be constructed for a variety of sensors. Consequently, the mesh characteristics are dependent upon the specific application, e.g., actual operating environment and conditions, and gas(es) to be sensed. Typically, the mesh comprises wire(s) woven, knitted, or the like, to form a sheet, tube, cylinder or the like. The mesh hole size should be sufficient to allow the desired flow of gas that is to be sensed to penetrate the mesh, while simultaneously protecting the lower end 82 of the sensing element. Since the gas pathway size is directly proportional to the wire diameter, the diameter can be chosen to control the gas flow to the sensor element. Generally, a wire having a diameter of up to about 0.5 millimeters (mm) or so can be employed, with a diameter of about 0.1 to about 0.3 mm preferred, and a diameter of about 0.15 to about 0.25 mm especially preferred.

Similarly, altering the density of the mesh design can also control the quantity of gas introduced to the sensor element. Densities of about 4 grams per milliliter (g/ml) to about 8 g/ml can be employed, with densities of about 5 g/ml to about 7 g/ml typically preferred for most engine types. For example, for a gas engine, a high nickel content steel wire having a diameter of about 0.0106 inches can be knit to form a tube. The tube can be folded over to create two layers. The layered, knit mesh can then be compressed to the desired cap shape and a density of about 5.8 g/ml. A similar mesh cap having a density of about 6.3 g/ml can be formed for a diesel engine sensor using an 0.009 inch diameter wire.

Generally, mesh material 31 comprises multiple layers which create a tortuous gas path. For example, a sheet of metal mesh can be folded once or several times in and upon itself. One advantage to a multilayered mesh material 31 is that an increased heat conduction pathway is created, thereby avoiding problematic heat effects upon the lower end 82 of the sensing element. Although heat conduction will occur from wire layer to wire layer in a folded arrangement because the wire to wire contacts are point to point, the thermal transfer is not significant. In other words, the amount of surface area contacting between the layers is much smaller than the total surface area of the mesh, which thereby allows for easier temperature regulation of the sensor element.

Prior to disposing the mesh material 31 over the sensing element, the mesh material can be coated with a material capable of filtering and or catalytically reacting with the exhaust gas. For example, the mesh material can be coated with a metal (including but not limited to, noble metals, alkali and alkaline earth metals, rare earth metals, and alloys and combinations comprising at least one of the foregoing), metal oxide, and the like, as well as alloys and combinations comprising at least one of the foregoing metals or metal oxides, using any conventional coating technique such as dipping, spraying, vapor deposition, and the like. Some possible materials include platinum, palladium, rhodium, iridium, osmium, ruthenium, alumina, zirconia, ceria, titania, lanthanum oxide, and the like, and alloys and combinations comprising at least one of the foregoing materials, with platinum, palladium, rhodium, alumina (such as alpha alumina, gamma alumina, delta alumina, and the like), and alloys and combinations thereof.

Referring to FIG. 3, an above planar view of protective shield 30 is shown. The mesh material 31 is formed as a cap so that upon being affixed to the gas sensor, lower end 82 of the sensing element is surrounded and positioned within the open space of protective shield 30.

Unlike the mesh shield, the majority of the gas that enters the outer shield of the prior art dual shield (as much as about 90%) never contacts the lower end of the sensing element. The majority of the gas simply travels through the space between outer shield and internal shield, diminishing the thermal isolation of the internal shield from exhaust gas temperatures, and requiring more energy to keep the sensor at proper operating temperature. Additionally with the dual shield, it is difficult to remove contaminants from the exhaust gas using a catalyst or poison-trapping coating placed upon the dual shield's surfaces. This is because the majority of gas passing through the dual shield does not actually contact the walls of the shield.

With a mesh shield, an advantageous gas sampling technique is achieved. Because mesh material 31 is porous, gas is allowed to enter the interior of protective shield 30. In passing through mesh material 31, the gas must transverse a tortuous path to reach the lower end 82 of the sensing element. This causes the gas to contact a significant amount of mesh surface area. This allows a coating on the mesh material to treat the gas before reaching the sensor element. For example, in diesel exhaust, sensors can have significant particulate build up on the internal shield of a prior art dual shield, which can plug apertures changing the amount of flow entering the shield. By coating the mesh with an oxidizing catalyst, for example, particulate build up can be oxidized keeping the mesh shield clean.

A variation is provided by using the beneficial mesh to combine mesh with protective shields. An example of an alternative is depicted in FIGS. 4 and 5 wherein mesh material 31 is placed between outer shield 34 and internal shield 35 of a dual shield protective shield 30. The design would allow gas to enter through one or more apertures 38 in outer shield 34, pass through mesh material 31, and contact lower end 82 of the sensing element after passing through one or more apertures 39 of internal shield 35. Having mesh disposed between outer shield 34 and internal shield 35 provides a tortuous pathway wherein a majority of the gas entering the protective shield 30 will contact the lower end 82 of the sensing element. As shown in FIG. 5, apertures 38 and 39 are preferably skewed to provide additional control of the amount of gas flow entering the interior of protective shield 30. Another alternative design (not depicted) is to have mesh material 31 replace internal shield 35 entirely. These variations advantageously reduce the amount of by-pass flow around the inner portion of the protective shield as compared to a traditional dual shield.

Referring to FIG. 6, an example of exhaust sensor implementing protective shield 30 as shown in FIG. 2. An exhaust sensor 10 is shown having a protective shield 30 comprising a mesh material 31. The sensor 10 includes a housing structure generally formed of an upper shield 20, an inner shield 40, and a shell 50 with a protective shield 30, comprising a mesh material 31, disposed at an end of shell 50 opposite upper shield 20. A terminal connector 60 and a portion of a sensing element 80 are disposed within upper shield 20. Sensing element 80 is a pumped-air reference exhaust sensing element of a known type with any conventional geometry, such as a generally flat elongated rectangular shape. At a lower end 82 thereof, sensing element 80 includes an exhaust constituent-responsive structure, e.g., an electrochemical cell, fabricated into sensing element 80 in a known manner, preferably along with a heater (not shown) of a known type.

At an upper end 84 of sensing element 80, terminals 100 and 102 are electrically connected to contact external pads (not shown) on upper end 84 to provide electrical connection between terminals 100 and 102 and sensing element 80. Preferably, terminals 100 and 102 comprise spring terminals, the use of which is known in the art and the compressive force generated by disposing end 84 between spring terminals 100 and 102 securely maintains end 84 in electrical contact therewith.

The inner shield 40 has a first end 42 and a partially closed second end 44 opposite first end 42. Disposed within inner shield 40 is a central portion of sensing element 80, and a high temperature mat 90 that can be concentrically disposed around sensing element 80. As used herein, the term "high temperature mat" refers to materials that are designed for use in a spark ignition engine environment, where temperatures range up to about 1,000° C. Such materials include ceramic fibrous materials and/or metal mesh, among others.

Shell 50 includes a body portion 52 and a threaded portion 54 at a second end 55. Body portion 52 is preferably shaped to accommodate a wrench or other tool for tightening threaded portion 54 into a mount for an exhaust pipe or other component of an exhaust flow system enabling a sensor protective shield 30 to be located within a flow of exhaust gasses to be measured. A top portion of shell 50 can be disposed proximate to a lower end of the upper shield 20 when shell 50 is securely disposed around inner shield 40 by means known in the art; and preferably, shell 50 is coupled to upper shield 20. Shell 50 can itself be securely coupled to upper shield 20 by crimping or otherwise affixing shell 50 thereto. Alternatively, both shell 50 and upper shield 20, individually, can be securely coupled to inner shield 40 by crimping or otherwise affixing.

In a generally preferred configuration, mesh material 31 is securely coupled to shell 50 by engaging an open end of mesh material 31 with an aperture 58 in shell 50. Since sensing element 80 extends from upper shield 20 through shell 50, extending out of the second end 55, lower end 82 of sensing element 80 is disposed within a sensing chamber within protective shield 30.

At the opposite end of the sensing pair of electrical terminals 100 and 102 are adapted to be connected to electrical wires 120 and 130 in a known manner. Electrical wires 120 and 130 pass through cable seal 140, which generally comprises an elastomeric material suitable for use in a high temperature environment, e.g., spark ignition engine, without prematurely failing. Cable seal 140 is maintained at an upper end of upper shield 20, wherein upper shield 20 is typically crimped in place around cable seal 140 to further secure the same.

For the structures shown in FIG. 6, exemplary materials for the shields 20, 40, and for the shell 50 are high chrome, high nickel stainless steel, and mixtures comparing at least one of the foregoing materials and the like with all steels chosen for high temperature endurance, high-strength and corrosion resistance. Terminal connector 60 may be formed of a thermoplastic or thermoset material (e.g., plastic) or ceramic durable in the high temperature environments to which exhaust sensor 10 is exposed.

The protective shield disclosed herein uses a mesh material to form the cavity around the sensing element, in place of, or in combination with, single or dual protective shields. Where only the mesh is employed, there is substantially no waste material generated that would otherwise be created by punching apertures into the sheet metal portions typically used to form protective shields. Also, since the tooling of mesh material can be easily adjusted for differently shaped protective shields, tooling costs are reduced as compared to that required with sheet metal use.

With use of the mesh material, flow to the sensor element is improved. First, the placement of the shield is not orientation sensitive to the flow of exhaust gas because the mesh is porous over its entirety. Second, the amount of gas flow that flows into the outer shield and bypasses the internal shield of the protective shield is minimized, and therefore, the thermal isolation of the inner portion is increased. Thermal isolation is preferred to maintain the sensor element at the desired temperature to avoid inaccurate sensor readings resulting from the temperature fluctuations. Third, the mesh can be covered with coatings to alter or filter the exhaust before it reaches the sensor element. Because the mesh has a much greater surface area as compared to sheet metal shields, and since a torturous gas path can be created, shield coatings are effective. Hence, the amount of contamination, e.g., poisons and build up about the shield, is minimized.

While preferred embodiments have been shown and described, various modifications and substitutions may be made thereto without departing from the spirit and scope of the invention. Accordingly, it is to be understood that the present invention has been described by way of illustration and not limitation.

What is claimed is:

1. An exhaust gas sensor, comprising:
   a protective shield having a one piece structure of a porous mesh material configured to cap one end of the sensor; and a sensing element having a first end and a second end, whereby the second end extends into a cavity defined by the protective shield and is encased in the cavity, the second end of the sensing element in fluid communication with an external gas stream, fluid communication between the external gas stream and said sensor element consists of passage through said mesh material defining an exterior of at least a lower portion of the sensor in direct communication with the gas stream to the second end.

2. The exhaust gas sensor of claim 1, wherein the mesh material is cupped having a multilayer wall structure defining a cup having an opening at one end thereof to receive the second end of the sensing element, the multilayer wall structure formed by folding the mesh material along a perimeter defining the opening.

3. The exhaust gas sensor of claim 2, wherein the multilayer wall structure comprises a unitary piece of the mesh material that is folded in and upon itself to form the layers around the cup.

4. The exhaust gas sensor of claim 1, wherein the mesh material is stainless steel.

5. The exhaust gas sensor of claim 4, wherein the mesh comprises a wire having a thickness of about 0.1 to about 0.3 mm.

6. The exhaust gas sensor of claim 1, wherein the mesh material provides a tortuous passage way for gas to be sensed by the sensing element.

7. The exhaust gas sensor of claim 1, wherein the mesh material further comprises a coating selected from the group consisting of noble metals, alkali metals, alkaline earth metals, rare earth metals, metal oxides, and alloys and combinations comprising at least one of the foregoing coatings.

8. The exhaust gas sensor of claim 7, wherein the coating is selected from the group consisting of platinum, palladium, rhodium, iridium, osmium, ruthenium, alumina, zirconia, ceria, titania, lanthanum oxide, and alloys and combinations comprising at least one of the foregoing.

9. The exhaust gas sensor of claim 1, wherein the porous mesh material has a density of about 4 g/ml to about 8 g/ml.

10. The exhaust gas sensor of claim 9, wherein the porous mesh material has a density of about 5 g/ml to about 7 g/ml.

11. A method of making an exhaust gas sensor, comprising:
    forming a protective shield having a one piece structure of a porous mesh material configured to cap one end of the sensor; and
    disposing at least a sensing portion of a sensing element within the protective shield, fluid communication between an external gas stream and the sensing portion consists of passage through said mesh material defining an exterior of at least a lower portion of the sensor in direct communication with the gas stream to the second end.

12. The method of making an exhaust gas sensor of claim 11, wherein forming the mesh material further comprises cupping the mesh material to form a multilayer wall structure defining a cup having an opening at one end thereof to receive the sensing portion, the multilayer wall structure formed by folding the mesh material in and upon itself to form at least two layers around the cup.

13. The method of making an exhaust gas sensor of claim 11, further comprising coating the mesh material, wherein the coating is selected from the group consisting of noble metals, alkali metals, alkaline earth metals, rare earth metals, metal oxides, and alloys and combinations comprising at least one of the foregoing coatings.

14. The method of making an exhaust gas sensor of claim 13 wherein the coating is selected from the group consisting of platinum, palladium, rhodium, iridium, osmium, ruthenium, alumina, zirconia, ceria, titania, lanthanum oxide, and alloys and combinations comprising at least one of the foregoing.

15. A method of using an exhaust gas sensor, comprising:
    disposing the sensor within a gas stream, wherein the sensor comprises a protective shield having a one piece structure of a porous mesh material configured to cap one end of the sensor and a sensing element whereby a second end of the sensing element extends into a cavity defined by the protective shield and is encased in the cavity, the second end of the sensing element is fluid communication with an external gas, the fluid communication between the external gas stream and the sensing element consists of passage through said mesh material defining an exterior of at least a lower portion of the sensor in direct communication with the gas stream to the second end;
    passing the gas stream through the mesh material to the cavity of the protective shield;
    exposing the sensing element to the gas stream; and
    contacting at least one electrochemical cell within the sensing element with the gas steam.

16. A method of using an exhaust gas sensor as in claim 15, further comprising passing the gas through a torturous path of the mesh material.

17. A method of using an exhaust gas sensor as in claim 16, wherein the mesh material has a density of about 4 g/ml to about 8 g/ml.

18. A method of using an exhaust gas sensor as in claim 17, wherein the porous mesh material has a density of about 5 g/ml to about 7 g/ml.

* * * * *